United States Patent [19]
Kross

[11] Patent Number: 5,820,822
[45] Date of Patent: Oct. 13, 1998

[54] ANTIMICROBIAL COMPOSITION AND METHOD OF USE

[76] Inventor: Robert D. Kross, 2506 Florin Ct., Bellmore, N.Y. 11710

[21] Appl. No.: 738,006

[22] Filed: Oct. 25, 1996

[51] Int. Cl.⁶ ..................................................... A61K 7/20
[52] U.S. Cl. ................................. 422/37; 424/53; 424/66; 424/67; 424/685
[58] Field of Search .............................. 422/37; 424/53, 424/66, 67, 685

[56] References Cited

U.S. PATENT DOCUMENTS

| | | | |
|---|---|---|---|
| 4,084,747 | 4/1978 | Alliger | 239/4 |
| 4,945,992 | 8/1990 | Sacco | 166/310 |
| 5,122,282 | 6/1992 | Mason | 210/754 |
| 5,135,623 | 8/1992 | Dziabo et al. | 204/101 |
| 5,324,477 | 6/1994 | Schroeder et al. | 422/37 |
| 5,567,405 | 10/1996 | Klatte et al. | 423/477 |

*Primary Examiner*—Edward J. Cain
*Attorney, Agent, or Firm*—Edwin D. Schindler

[57] ABSTRACT

An antimicrobial and deodorizing composition is disclosed, which includes an aqueous solution having at least one acid-inducing metal salt and a metal chlorite and no protic acid. The aqueous solution has a pH less than about 7. The acidity-inducing metal salt, preferably, includes a iron cation, an aluminum cation, a gadolinium cation, a vanadium cation, a zirconium cation or a zinc cation, and anions sufficient for rendering said metal salt electrically neutral and water-soluble. The metal chlorite may, preferably, be sodium chlorite. Various methods for use of the composition are also disclosed.

17 Claims, No Drawings

ANTIMICROBIAL COMPOSITION AND METHOD OF USE

TECHNICAL FIELD

This invention relates generally to the use of metal salt activators of metal chlorites, to create disinfecting compositions containing chlorous acid and related oxychlorine species. The invention also provides methods for using such compositions to achieve optimum antimicrobial effects.

BACKGROUND OF THE INVENTION

In the last two decades, the disinfecting capabilities of the family of oxychlorine species has become increasingly understood and utilized. The term "disinfectant" is used in this specification to broadly include any substance or composition, stable or transient, that disinfects, sanitizes, sterilizes, and/or deodorizes materials or surfaces containing germs. The term "germs" includes bacteria, yeasts, molds, viruses or any micro-organism whose presence, and numbers, are deemed inimical to human or animal welfare.

For over fifty years the antimicrobial qualities of the oxychlorine compound chlorine dioxide have been investigated and used for such areas as water disinfection, area fumigation and food disinfection. Most frequently, the chlorine dioxide used for such purposes has been generated in an aqueous medium by combination of a chlorite salt with a strong mineral acid or a large amount of a moderately-strong organic acid. These combinations create conditions where a significant portion of the chlorite anion ($ClO_2^-$) is converted to unstable chlorous acid, which then undergoes a series of disproportionation reactions which result in the formation of chlorine dioxide and lesser amounts of chloride and chlorate ion. In 1978 Alliger in U.S. Pat. No. 4,084,747, and its reissue Re. 31,779 in 1984, showed that the use of a lesser quantity of a weaker acid, specifically lactic acid, in combination with aqueous chlorite ion, created a solution of high antimicrobial effectiveness. This solution, in addition to chlorine dioxide, included chlorous acid as a component of the germ killing composition. In a subsequent patent, U.S. Pat. No. 4,330,531 in 1982, Alliger incorporated the lactic acid/chlorite combination into more viscous or solid germ-killing formulations. Thereafter Tice et al., in U.S. Pat. No. 4,585,482 in 1986, disclosed a long-acting biocidal composition comprised of poly(lactic acid), or similar polymers from glycolic or maleic acid, and a chlorite salt, whereby subsequent exposure to moisture would hydrolytically create levels of lactic acid, or its analog, from the polymer, at a pH below 7, which acidity would be sufficient to form antimicrobial compositions with the chlorite.

U.S. Pat. No. 4,891,216, issued to Kross and Zamojcin in January 1990, discloses the use of protic acids, such as lactic acid, in combination with a metal chlorite and a polysulfonic acid polymer, to create a disinfecting protective skin barrier, where the level of protic acid is restrictively selected such that no more than about 15% of the chlorite anion is converted to its corresponding chlorous acid form. At that maximum level of formation, the chlorous acid is capable of remaining sufficiently stable so that it can act as a source of antimicrobial activity. Thereafter U.S. Pat. No. 4,956,184 issued to Kross in September 1990, teaches the use of protic acid-activated chlorite formulations for the treatment of genital herpes. In the disclosed systems, the protic acid has a $pK_a$ of from about 2.8 to about 4.2, so that the chlorite ion concentration in the form of chlorous acid is no more than about 15% of the total amount of chlorite. Again, higher levels of acidity would create higher levels of the unstable chlorous acid, resulting in enhanced rates of formation of chlorine dioxide. The Davidson and Kross patents, U.S. Pat. Nos. 4,986,990 and 5,185,161, which respectively issued in Jan. 22, 1991 and Feb. 9, 1993, disclosed chlorous acid generating compositions useful for disinfecting substrates, where organic acids with $pK_a$'s in the 2.8–4.2 range were selected to effect conversions of no more than about 15% of the chlorite anion to chlorous acid. These organic acid/chlorite compositions were then found to have application to oral hygiene, as taught by U.S. Pat. No. 5,100,652 issued to Kross et al. in March 1992, again with the 15% maximum conversion of chlorite to chlorous acid. Subsequent to that, Lukakovic and Majeti, in U.S. Pat. No. 5,281,412 issued in January 1994, taught the use of antimicrobial oral compositions containing a chlorous acid liberating compound comprised of a metal chlorite and the citrate ion, at an acidic pH of from about 5.9 to about 6.5.

A lactic acid-activated chlorite composition and method for cleaning, disinfecting and sterilizing used hemodialyzers was disclosed by Aixalá, U.S. Pat. No. 5,178,830 which issued in January 1993. A related composition for sterilizing hemodialyzers was taught by Tell, in U.S. Pat. No. 5,192,459, where the sterilant was comprised of sodium chlorite and an acid, such as citric acid, buffered to about pH 7.3. Anti-inflammatory organic-acid activated chlorite compositions were then disclosed by Kross and Siff, in U.S. Pat. No. 5,384,134 which issued in January 1995. The organic acids were again confined to $pK_a$ values of about 2.8 to about 4.2, and the resulting chlorous acid represented no more than about 15% of the total chlorite in free and acidified forms. An acidified chlorite composition was thereafter disclosed by Kross, in U.S. Pat. No. 5,389,390 issued in February 1995, as a process for removing bacteria from poultry and other meats. The acid concentration was adjusted so that the disinfecting composition had a pH of from about 2.2 to 4.5, and the chlorous acid formed thereby represented no more than about 35% of the total chlorite in free and acidified forms.

In all of these disinfecting oxychlorine-containing compositions the biocidally-active chlorous acid, and any chlorine dioxide subsequently-formed from the chlorous acid decomposition, all derive from combinations of a metal chlorite and a protic acid, i.e. an inorganic or organic acid capable of ionizing and donating an $[H]^+$ ion [a proton]. The latter combines with the chlorite anion $[ClO_2]^-$ to form chlorous acid $[HClO_2]$. There are certain circumstances, however, where it would be desirable to create compositions containing chlorous acid and/or its degradation product chlorine dioxide without the need for proton-donating acids in the composition, or where the direct use of acids is counterindicated. Some of these areas are further described later in this application. A search was undertaken to determine if chlorous acid, and the resulting disinfecting oxychlorine degradation products including chlorine dioxide, could be created without the direct inclusion of a proton-donating acid in metal chlorite-containing compositions. This invention was made as a result of that search.

OBJECTS AND SUMMARY OF THE INVENTION

Accordingly, it is a general object of the present invention to substantially alleviate the above-identified deficiencies of the prior art.

A specific object of the present invention is to provide disinfecting and deodorizing metal-chlorite compositions which can induce the formation of chlorous acid and its ensuing oxychlorine degradation products without the direct inclusion of protic acids in the composition.

A further object of the present invention is to provide methods for utilizing those disinfecting or deodorizing compositions in situations where the presence of protic acids is not desirable, or counterindicated.

Other objects and advantages of the present invention will become apparent from the following summary of the invention and description of the preferred embodiments.

The present invention provides in one aspect, a method for disinfecting substrates in which a metal chlorite is combined with selected metal salts which are capable of inducing an acidic environment in an aqueous or water-absorbing matrix. These salts create an imbalance between the free hydroyl [OH]$^-$ and hydrogen [H]$^+$ ions normally present in water, by interacting with and thereby reducing the number of [OH]$^-$ ions in the aqueous medium, such that there is a relative excess of [H]$^+$ ions. These [H]$^+$ ions can then react, in some measure, with the chlorite ion formed from dissociation of the metal chlorite in the aqueous medium, to form chlorous acid.

In another aspect, the present invention provides a method for incorporating such metal salts into selected aqueous and non-aqueous environments, for subsequent creation of chlorous acid, and related successive oxychlorine disinfecting and deodorizing species.

In a further aspect, the present invention provides compositions of metal salts and metal chlorite salts which, when combined in the presence of water, will interact to create the additional species chlorous acid, in an amount so as to be substantially effective as a disinfectant and/or a deodorant.

In one embodiment, a deodorizing composition of this invention is applied to the surface of the skin to reduce the level of topical microorganisms associated with malodor. In another embodiment, a composition is introduced into the oral cavity to reduce bad breath and the levels of microbes which cause dental plaque and gum disease. In yet another embodiment, the dry metal salts and metal chlorite salts are contained in a non-aqueous packaging film, such that subsequent absorption of moisture from the package environment will result in the creation of chlorous acid and its subsequent gaseous degradation product chlorine dioxide, which then disinfects the package contents.

These and other aspects of this invention will become evident upon reference to the following detailed description.

DETAILED DESCRIPTION OF THE INVENTION

The present invention provides compositions and methods for creating disinfecting and deodorizing chlorous acid [$HClO_2$] and chlorous-acid derived oxychlorine species from metal chlorite salts without utilizing proton-donating acids. The chlorous acid in aqueous solutions provides its oxidative disinfecting and deodorizing action through a series of transient and stable oxychlorine degradation species. These include hypochlorous acid [HOCl], dichlorine dioxide [$Cl_2O_2$], and chlorine dioxide [$ClO_2$]. The chlorine dioxide/chlorite complex anion [$Cl_2O_4$]$^-$ is also believed to provided antimicrobial and deodorizing properties.

The formation of aqueous acidic environments can be brought about by the interaction of selected metal salts and water. For example, certain hydrated metal salts, such as iron, aluminum and gadolinium chlorides, will replace a bound water with an hydroxyl radical [OH]$^-$ from the water mediums which essentially liberates a free proton into the aqueous environment. The following representative reactions of the respective hydrated cations illustrate these mechanisms. The effective $pK_a$'s of these reactions, which indicate the degree of acidity created by dissolution of these salts, are given after each reaction.

IRON $[Fe(H_2O)_6]^{3+} \leftarrow\rightarrow [Fe(H_2O)_5(OH)]^{2+} + H^+ \; pK_a = 3.05$ $[Fe(H_2O)_6]^{2+} \leftarrow\rightarrow [Fe(H_2O)_5(OH)]^{1+} + H^+ \; pK_a = 3.26$ $2[Fe(H_2O)_6]^{3+} \leftarrow\rightarrow [Fe(H_2O)_4(OH)_2Fe(H_{2O},4)]^{4+} + 2H^+ \; pK_a = 2.91$

GADOLINIUM $[Ga(H_2O)_6]^{3+} \leftarrow\rightarrow [Ga(H_2O)_5(OH)]^{2+} + H^+ \; pK_a = 2.60$

ALUMINUM $[Al(H_2O)_6]^{3+} \leftarrow\rightarrow [Al(H_2O)_5(OH)]^{2+} + H^+ \; pK_a = 4.96$

VANADIUM

The vanadyl cation, derived from the metal vanadium, also has a tendency to create an acidic aqueous environment, based on the tendency for the vanadyl species to polymerize, i.e.

$10VO_2^+ + H_2O \rightarrow H_2V_{10}O_{28}^{-4} + 14H^+$

ZIRCONIUM

Another metallic salt, zirconium oxychloride [$ZrOCl_2$] is known to create very acidic conditions upon dissolution in water. The Merck index states that the pH created by this salt is the same as for an equimolar amount of hydrochloric acid. For example, to achieve a pH of 3, one could use either 0.001N HCl or a solution of 0.0178% zirconium oxychloride.

It is also well known that the soluble salts of such metals as zinc, cadmium and magnesium create acidic conditions in aqueous media. Such salts would include, but not be limited to the following anions: chloride, nitrate, sulfate, perchlorate, acetate, citrate, and lactate.

Representative acidities of aluminum salt solutions are as follows: Aluminum acetate—1:20 pH 4.2; aluminum ammonium sulfate—0.05M (1.18%) pH 4.6; aluminum chlorhydroxide—15% solution pH 4.3. The latter salt is used extensively in underarm antiperspirants; and the inclusion of an encapsulated metal chlorite salt in an aluminum chlorhydroxide matrix, for release through application of pressure or body heat, will create an effective underarm deodorant in the acidic antiperspirant environment. Illustrative of the acidities of current commercial solid antiperspirant products are the following pH figures for 1% aqueous dispersions of these materials:

Sure: 4.03 Ultra Ban: 4.14 Arrid: 4.54 Brut: 4.55 Pierre Cardin: 4.59

All of these products predominate in aluminum chlorhydroxide as the active agent, with a concentration generally of about 20% (w/w).

In many underarm antiperspirants the aluminum chlorhydroxide is often present in a stable water-soluble complex in combination with propylene glycol, this complex being termed Rehydrol. Other aluminum salts, and their levels of use, are the sulfate (8%–20% in lotions and creams), the chloride (about 5% in creams and lotions), and the phenolsulfonate (about 10%–20%). All of these aluminum salts will induce acidic environments in aqueous media sufficient to form chlorous acid when a metal chlorite is introduced.

Zirconium salts are also effective antiperspirants, and are often used in combination with aluminum salts in underarm products. In addition to zirconium oxychloride, zirconium lactate and sodium zirconium lactate are effective antiperspirants. Their ordinary use levels are about 3% to 12%, which are also appropriate concentrations to create antimicrobially-effective amounts of chlorous acid. It is not necessary, however, to use these metal salts in high enough amounts to create effective antiperspirancy, in order to have sufficient acidity to form effective deodorants. In facts, while many people are irritated by the acidity of antiperspirant formulations, they may not be so affected by the lower levels of metal salts needed to create chlorous acid antimicrobial action.

In general, the use levels of these acid-inducing salts, for underarm deodorancy, range from about 1% to about 30%, depending on the nature, the molecular weight and the degree of hydration of the product. In preferred embodiments, the concentration, of the aluminum salts and the zirconium salts, individually or in combinations range from about 3% to about 20%. The concentration of the metal chlorite, upon combination with the acid-inducing metal salt, is generally about 0.05% to about 5%. Since the chlorite cannot be directly introduced into the aqueous metal salt environment without immediate formation of unstable chlorous acid, it must be included in the matrix in an encapsulated form, for subsequent release upon the skin. This may be immediately upon application to the body or some time afterwards. The capsule can contain a liquid concentrate or a metal chlorite powder, and be constructed of an impervious composition. In one embodiment, the capsule may be fabricated of a frangible material, such as a polyethylene wax, a natural material such as beeswax, a synthetic material such as Epolene or Acrawax, or a combination of these materials. Additional materials, such as titanium dioxide powder, may be included in the capsule walls to enhance frangibility. Upon application to the skin, the capsules are broken by the pressure of the application, and they release their contents to the acidic environment created by the aqueous metal salts.

In another embodiment, the capsule walls are comprised of meltable, water-insoluble polymers, with melting points approximately the same as body temperature. After application to the skin in a gelled metal salt matrix, the capsules are warmed by the body, and melt. This process releases the capsules' metal chlorite solution or powder contents to the acidic environment. Typical compositions of these meltable capsules include the following materials, generally as mixtures, formulated to achieve the appropriate melting temperature and other necessary physical parameters: Microcrystalline wax, cocoa butter, myristyl myristate, hydrogenated castor oil, beeswax and beeswax substitutes, behenamide monoethylamine, hydrogenated castor oil, and mixtures of long chain fatty acids and glycerides. The metal chlorite is typically enveloped by these polymers by a coacervation process.

Zinc salts have found application in the oral care field, as effective antiplaque and anticalculus agents. They have also shown efficacy in reducing oral malodor. Zinc chloride and zinc citrate are the primary zinc salts that have been used in dentifrices and mouthwashes. Zinc chloride, for example, at a concentration of 0.25%, has a pH of about 4. Other zinc salts which induce acidic environments include zinc nitrate (where a 5% solution has a pH of about 5.1) and zinc sulfate (where a saturated solution has a pH of about 4.5). The aqueous combination of a zinc salt, such as zinc chloride, and a metal chlorite salt, such as sodium chlorite, is an effective treatment for oral malodor, as well as being helpful in reducing dental plaque, calculus formation, and inflamed oral surfaces. In general these combinations of metal chlorite and acid-inducing metal salt must be prepared shortly before use, to prevent undue degradation of the chlorous acid that is immediately formed. The mixed solution is generally comprised of zinc salts in the range from about 0.05% to about 0.5%, preferably from about 0.15% to about 0.35%, and most preferably from about 0.2% to about 0.3%. The metal chlorite, in a preferred embodiment, is sodium chlorite, at a concentration range of about 0.05% to about 0.35%, and most preferably from about 0.1% to about 0.2%. Additional components such as flavor, bodying agents, colors and sweeteners may be included in one or both of the premixed metal salt and metal chlorite solutions, in order to provide appropriate consumer acceptability.

Another application in which it is difficult to use proton-donating acids to activate a chlorite to chlorous acid is in packaging materials. The acid, or even precursor acid anhydride, causes rapid chlorite decomposition. In this invention a metal chlorite salt, instead of a proton-donating material, is incorporated into a dry polymer or oligomer film in combination with a selected anhydrous metal salt. An anhydrous deliquescent salt may be optionally included into the matrix. Upon exposure to a moist environment, the film will absorb moisture into itself, and the metal salt will induce an acidic environment by preferentially attracting $[OH]^-$ radicals into its immediate structure. The chlorous acid, thus formed, will partially degrade to chlorine dioxide, the vapors of which can act as a microbiocide and deodorant. The packaging film can be so constructed that the outer portion will have a low permeability to chlorine dioxide gas, such as from a polyvinylidene chloride or polyester film, so that the gas generated will preferentially diffuse inwards to the packaged contents. The metal chlorite may be contained in films such as described by Wellinghoff (U.S. Pat. No. 5,360,609) which is incorporated herein by reference. In that patent, the metal chlorite is suspended in a hydrogen bonded matrix, such as a mixture of formamide, acrylamide and isopropylacrylamide. In the Wellinghoff patent, that phase is mixed with a phase containing a hydrolyzable acid anhydride, from which mixture a sustained release of chlorine dioxide is observed within five minutes. In contrast, in the present patent, a similar hydrogen bonded phase is mixed with a phase containing a specific anydrous metal salt dispersed in an organic solvent solution of a polymer From this mixture no chlorine dioxide will evolve, even when the solvent mixture is deposited by evaporation onto a barrier film surface. The concentration of metal chlorite salt in the hydrogen bonded matrix is preferably in the concentration range of about 1% to 14 wt %, and the total dissolved polymer is preferably in the range of about 50% to about 80%. This phase may be preferably combined with the metal chlorite phase in a ratio of about 1:2 to about 2:1. The metal salt in the anhydrous, apolar phase is preferably in the concentration range of about 0.5% to about 10% and the polymer component of that phase is preferably in the concentration range of about 50% to about 75%. After deposition of that phase onto a carrier film, no evolution of chlorine dioxide is observed to occur through degradation of chlorous acid until the barrier film is exposed to an environment from which moisture in the air can induce an acidic environment brought about by the dissolution of the metal salts in the film. The metal salts may comprise, but not be limited to, one or a combination of the water soluble metal salts of such cations as aluminum, ferric, ferrous, cadmium, gallium, zirconyl, vanadyl, stannous, stannic, and zinc, in combination with appropriate anions.

It should be noted that the use of such metal salts as sole activators of metal chlorites to form disinfecting chlorous acid, as well as chlorine dioxide under some circumstances, differs substantially from the use of transition metals and metal oxides to enhance the catalytic generation of chlorine dioxide from sodium chlorite, as taught in Ringo, U.S. Pat. No. 5,008,096 in 1991. In that patent, certain metals were to used to stimulate higher levels of chlorine dioxide generation when they were included in well-known oxidation or acidification reactions by which chlorine dioxide is formed from sodium chlorite.

The present invention is illustrated by the following examples. Unless otherwise noted, all parts and percentages in the examples as well as the specification and claims are by weight.

EXAMPLES

Example 1

This example illustrates the use of a representative deodorant stick, in which microencapsulated sodium chlorite solution is suspended in a gelled composition containing aluminum chlorhydroxide at a level below that which provides adequate antiperspirancy, but sufficient to induce the formation of chlorous acid from chlorite. Upon application of the stick to the underarm, the frangible capsules containing the chlorite solution are broken, releasing the capsule contents into the acidic aluminum salt medium.

An aluminum chlorhydroxide stick is prepared from the following ingredients:

| Part A | |
| --- | --- |
| Aluminum chlorhydroxide, 15% solution | 10.00 gm |
| Ethyl alcohol | 12.00 ml |
| Propylene glycol | 3.00 gm |
| Sodium hydroxide | 0.75 gm |
| Stearic acid | 5.25 gm |
| Water | 42.00 gm |
| Part B | |
| Microcapsules with the following characteristics | |
| Shell: | 80% Boler paraffin wax 1426 20% Epolene C-16 polyethylene |
| Fill: | 35% Aqueous sodium chlorite |
| Payload: | 40% |
| Size | 500 μM |
| Density: | 1.07 gm/ml |
| Burst strength: | 30–50 gm |

The stearic acid is dissolved in the glycol/alcohol mixture. In another container the sodium hydroxide is dissolved in the water and combined with the aluminum chlorhydroxide solution, which mixture is then heated to 65° C. The alcohol solution is heated in a separate container to the same temperature and added to the aqueous solution with stirring. The soap forms rapidly. When the reaction is complete, the mixture is cooled slowly until it begins to thicken, at which point 5 gm of the sodium chlorite microcapsules are stirred in carefully to a uniform dispersion. The product is then poured into a mold to further cool.

Example 2

This example illustrates the use of a representative deodorant cream, in which microencapsulated sodium chlorite solution is suspended in an oil water cream base containing a mixture of metal salts which induce formation of chlorous acid. Upon application of the cream to the underarm, the applied pressure releases the chlorite from the capsules, and the acid environment induces the creation of chlorous acid.

A cream base is prepared by mixing the following ingredients in the order listed, at 45°–50° C.:

| | |
| --- | --- |
| Glycerol | 10 gm |
| Sorbitan monostearate, polyoxyethylene derivative | 3 gm |
| Glyceryl monostearate | 13 gm |
| Triethanolamine salt of dodecylbenzene sulfonate | 10 gm |
| Spermaceti wax | 3 gm |
| Petrolatum | 1 gm |
| Water | 52 gm |
| Titanium dioxide | 1 gm |
| Sodium zirconium lactate | 5 gm |
| Aluminum chloride | 2 gm |

When the mixture is uniform, it is cooled slowly until it begins to thicken, at which point 6 gm of the sodium chlorite microcapsules from Example 1 are stirred in carefully, to form a uniform dispersion. The product is then poured into jars to cool, and capped.

Example 3

This example illustrate the use of a concentric deodorant stick, where the underarm application and abrasion of two separated solid phases, containing a specific metal salt in one phase and a metal chlorite salt in the other, causes the two phases to mix on the skin and create an antimicrobial and deodorizing chlorous acid matrix.

The aluminum chlorhydroxide stick in Example 1 is prepared without the inclusion of the sodium chlorite microcapsules. The stick is cooled to about 10° C. and a 2-cm central cylinder is removed with a cork borer. Into the hole that is formed is poured a melted paraffin wax, at about 40° C., which is then poured out after about 2 minutes. This leaves a thin wax coating over the inner surface of the hollow cylinder. Into this cavity is poured, up to the top surface of the stick, a composition of the following percent composition, preheated to 40° C.:

| | |
| --- | --- |
| Stearyl alcohol | 10 gm |
| Cyclomethicone | 20 gm |
| Isopropyl alcohol | 50 gm |
| Sodium stearate | 8 gm |
| Sodium chlorite (pure basis) | 1 gm |
| Sodium hydroxide, 1N | 2 gm |
| Water | 9 gm |

The combination is cooled to 15°–20° C., to set the inner phase.

Example 4

This example illustrates the use of a mixed metal salt to create an astringent, deodorizing and antimicrobial oral rinse. The rinse is prepared by combining equal volumes of the following two liquid phases directly before use:

| Phase A | |
|---|---|
| Zinc chloride | 0.10% |
| Aluminum potassium sulfate | 0.10% |
| Glycerin | 20.00% |
| Ethyl alcohol | 10.00% |
| Cinammon oil | 0.010% |
| Menthol | 0.050% |
| FD&C Red No. 40 | 0.002% |
| Water | 69.708% |
| Phase B | |
| Sodium chlorite (pure basis) | 0.25% |
| Water, q.s. after adding sodium hydroxide, to → | 100.00% |
| Sodium hydroxide 1N, q.s. to achieve solution pH = 10 | |

Example 5

This example illustrates the use of comixed, solvent-dispersed phases of a) metal chlorite salt+monomer, and b) acid-inducing metal salt+polymer, as a deposit on a packaging film, such that the resulting cured film creates chlorine dioxide from the chlorous acid precursor that is formed upon absorption of moisture from the package environment. The composition is prepared in two parts by mixing the following ingredients, and maintaining each at 0°–5° C. until mixing and depositing:

| Part A | |
|---|---|
| Sodium chlorite | 7.00% |
| Formamide (anhydrous) | 31.00% |
| Acrylamide (anhydrous, stabilized) | 31.00% |
| Isopropylacrylamide | 31.00% |
| Part B | |
| Polystyrene | 60.00% |
| Ethylbenzene | 40.00% |

The composition is sprayed onto the surface of a 2-mil thick polyvinylidene chloride (Saran) film, and cures as the solvent evaporates In use, the low gas-permeable Saran substrate is on the outer surface of the packaging composition, and only moisture from the packaged contents will induce the reaction, and the resulting chlorine dioxide so formed will preferentially diffuse inwards.

Example 6

This example illustrates the use of a stable, single phase of comixed powders of a metal salt and a metal chlorite which, upon the addition of water, forms a disinfecting and deodorizing chlorous acid system. The mixture is stored in a moisture-barrier package to prevent premature activation.

| | |
|---|---|
| Sodium aluminum sulfate, anhydrous powder | 0.71 gm |
| Sodium chlorite, technical grade, anhydrous powder | 0.71 gm |

The powders are physically intermixed, in a dry environment, and enclosed in a Saran package. Upon opening, the powder is added to ounce of tap water and the mixture is stirred for 10 seconds to dissolve. The resulting solution which has a pH of 3.77, and develops the distinctive odor and color of chlorine dioxide, can be used as a disinfectant for inanimate and animate surfaces, such as on medical equipment or as a teat dip, respectively.

Example 7

This example illustrates the use of the stable, single-phase mixture shown in Example 6 as an area deodorant, disinfectant or fumigant. The powdered contents of the package are transferred to a glass dish, which is then placed in an area which requires disinfection or deodorization. Moisture from the environment is absorbed into the powder, which undergoes the production of gaseous chlorine dioxide. The rate of moisture uptake and onset of action may be enhanced by inclusion of a deliquescent salt, such as anhydrous calcium chloride, in the powdered mixture.

It is clear that the present invention is well adapted to carry out the objects and achieve the ends and advantages mentioned therein. While currently preferred embodiments of the invention have been described for purposes of this disclosure, numerous changes may be made which will readily suggest themselves to those skilled in the art, and which are encompassed within the spirit of the invention disclosed, and as defined in the appended claims.

What is claimed is:

1. An antimicrobial and deodorizing composition comprising:
an aqueous solution including at least one metal salt having a cation selected from the group consisting of iron cation, aluminum cation, gadolinium cation, vanadium cation, zirconium cation, zinc cation and a combination thereof, and anions sufficient for rendering said metal salt electrically neutral and water-soluble, said aqueous solution further comprising a metal chlorite and containing no protic acid and having a pH of less than about 7.

2. The composition according to claim 1, wherein said metal chlorite is sodium chlorite.

3. The composition according to claim 2, wherein said metal salt includes a zinc cation.

4. The composition according to claim 1, further comprising a plastic film into which said metal salt and said metal chlorite are dispersed, whereby a subsequent diffusion of moisture from packaged contents creates chlorous acid and chlorine dioxide.

5. An antimicrobial or deodorizing antiperspirant product, comprising:
a composition comprising an aqueous solution including at least one acidity-inducing metal salt and a metal chlorite, said aqueous solution having a pH less than about 7, the metal chlorite being encased in protective microcapsules which are dispersed in a carrier medium comprising as the metal salt a member selected from the group consisting of an aluminum metal salt, a zirconium metal salt and a combination thereof, so that upon a subsequent compression or warming of the product on a person's skin, a rupturing of the protective microcapsules occurs which results in releasing the metal chlorite into the carrier medium comprising the metal salt, thereby forming an antimicrobial or deodorizing antiperspirant effect.

6. A method for disinfecting an inanimate or an animate surface, comprising the step of:
applying to a surface a composition comprising an aqueous solution containing an acidity-inducing metal salt and a metal chlorite and containing no protic acid, the aqueous solution having a pH of less than about 7 and a chlorite concentration partially in the form of chlorous acid, chlorous acid being no greater than about 25% by weight of the total chlorite concentration.

7. The method according to claim 6, wherein said metal salt is comprised of a cation selected from the group consisting of iron cation, aluminum cation, gadolinium cation, vanadium cation, zirconium cation, zinc cation and a combination thereof, and anions sufficient for rendering said metal salt electrically neutral and water-soluble.

8. The method according to claim 6, wherein said composition comprises a liquid prepared by an addition of water to a mixture of two dry salts, a first salt of said two dry salts being a metal salt and a second salt of said two dry salts being a metal chlorite, so that when the mixture of said two dry salts is dissolved in water, the pH of said composition becomes less than about 7 and said composition has a chlorite concentration partially in the form of chlorous acid which is no greater than about 25%, by weight, of total chlorite concentration.

9. The method according to claim 8, wherein said metal salt is comprised of a cation selected from the group consisting of iron cation, aluminum cation, gadolinium cation, vanadium cation, zirconium cation, zinc cation and a combination thereof, and an anion sufficient for rendering said metal salt electrically neutral and water-soluble.

10. The method according to claim 6, wherein the metal salt includes a zinc cation and said composition is applied within a person's mouth for treating oral malodor, plaque and gingivitis.

11. The method according to claim 10, wherein said metal salt is comprised of a cation selected from the group consisting of iron cation, aluminum cation, gadolinium cation, vanadium cation, zirconium cation, zinc cation and a combination thereof, and anions sufficient for rendering said metal salt electrically neutral and water-soluble.

12. A method for disinfecting packaged materials, comprising the step of dispersing two dry salts in a plastic packaging film, a first salt of said two dry salts being an acidity-inducing metal salt and a second salt of said two dry salts being a metal chlorite, so that diffusion of moisture into the plastic packaging film from material packaged in said plastic packaging film will create chlorous acid and chlorine dioxide.

13. The method according to claim 12, wherein said metal salt is comprised of a cation selected from the group consisting of iron cation, aluminum cation, gadolinium cation, vanadium cation, zirconium cation, zinc cation and a combination thereof, and an anion sufficient for rendering said metal salt electrically neutral and water-soluble.

14. An antimicrobial and deodorizing composition comprising:

an aqueous solution including at least one metal salt and a metal chlorite and containing no protic acid, said aqueous solution having a pH less than about 7; and, a plastic film into which said metal salt and said metal chlorite are dispersed, whereby a subsequent diffusion of moisture from packaged contents creates chlorous acid and chlorine dioxide.

15. The composition according to claim 14, wherein said metal chlorite is sodium chlorite.

16. The composition according to claim 15, wherein said metal salt includes a zinc cation.

17. An antimicrobial and deodorizing composition comprising:

an aqueous solution including at least one metal salt having a zinc cation and sodium chlorite and containing no protic acid, said aqueous solution having a pH less than about 7.

* * * * *